United States Patent [19]

Pink

[11] Patent Number: 4,673,656
[45] Date of Patent: Jun. 16, 1987

[54] AEROSOL PRODUCTION IN INDUCTIVELY COUPLED PLASMA EMISSION SPECTROSCOPY

[75] Inventor: Hans Pink, Starnberg/See, Fed. Rep. of Germany

[73] Assignee: Siemens Aktiengesellschaft, Berlin and Munich, Fed. Rep. of Germany

[21] Appl. No.: 747,957

[22] Filed: Jun. 24, 1985

[30] Foreign Application Priority Data

Jul. 11, 1984 [DE] Fed. Rep. of Germany ....... 3425549

[51] Int. Cl.$^4$ ............................................. G01N 21/73
[52] U.S. Cl. ...................................... 436/173; 422/68; 436/181; 261/DIG. 48; 261/81
[58] Field of Search ................................. 436/173, 35; 261/DIG. 48, 81; 422/68, 78

[56] References Cited

U.S. PATENT DOCUMENTS

| | | | |
|---|---|---|---|
| 4,087,495 | 5/1978 | Umehara | 261/DIG. 48 |
| 4,109,863 | 8/1978 | Olson et al. | 261/DIG. 48 |
| 4,524,746 | 6/1985 | Hansen | 261/DIG. 48 |
| 4,582,654 | 4/1986 | Karnicky et al. | 261/DIG. 48 |

OTHER PUBLICATIONS

Perkin-Elmer Information Sheft. 28, (1981) "III. Introduction to AES with an Inductively Coupled Plasma (ICP)".

"A Corrosion Resistant Sample Introduction System for ICP Emission Spectroscopy" presented in part at the Pittsburgh Conference on Analytical Chemistry and Applied Spectroscopy, Atlantic City, New Jersey, Mar. 8–12, 1982, Paper #157.

Drews, Wolf-Dietrichy, "Liquid Atomization By Means of Ultrasonics", reprint from *Elektronik* vol. 28, No. 10, 1979.

Primary Examiner—Michael S. Marcus
Attorney, Agent, or Firm—Hill, Van Santen, Steadman & Simpson

[57] ABSTRACT

Apparatus and method are provided for improving the sample aerosol yield in plasma-emission, sequential spectroscopic analysis. A reservoir is employed and an aerosol is produced therein from a limited amount of sample liquid with the assistance of an electro-mechanical oscillator system. Only that amount of aerosol which is supplied to an interconnected plasma by a carrier gas stream is used for a single analysis. Unused aerosol in the reservoir recondenses and mixed with residual sample liquid. Nearly 100% of a sample liquid may be used in this way.

6 Claims, 2 Drawing Figures

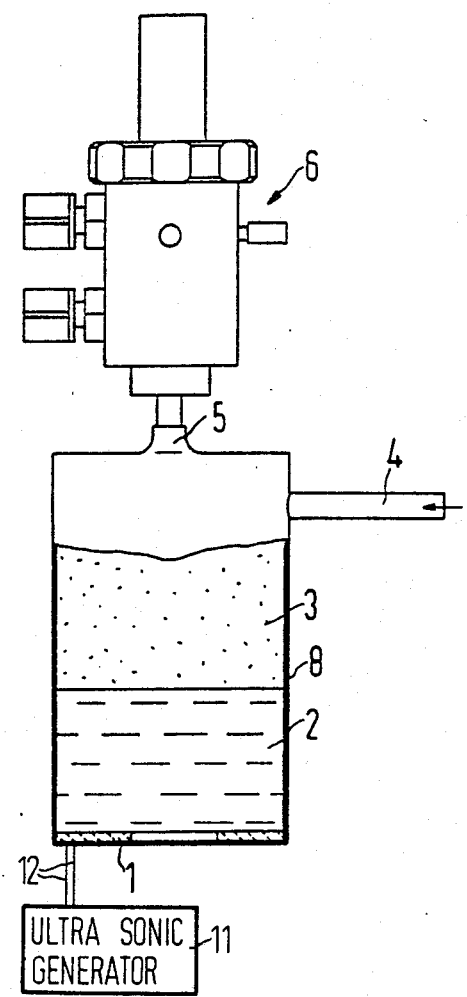
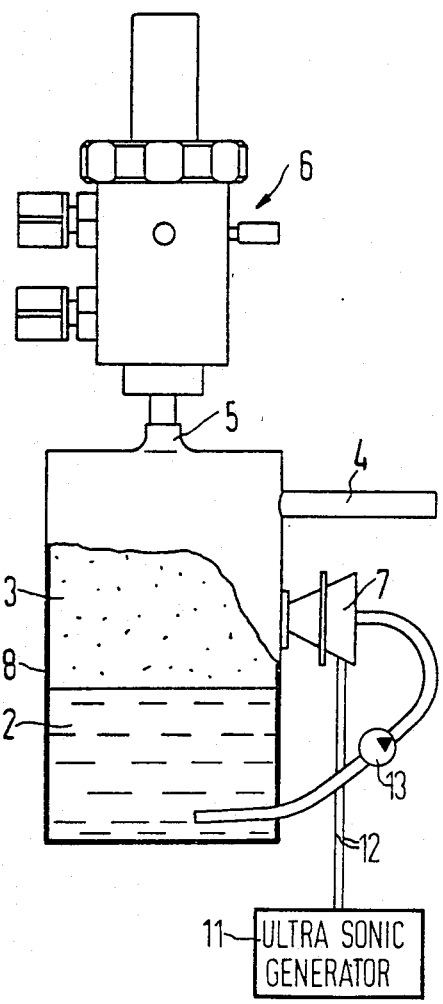

AEROSOL PRODUCTION IN INDUCTIVELY COUPLED PLASMA EMISSION SPECTROSCOPY

BACKGROUND OF THE INVENTION

1. Field Of The Invention

This invention lies in the field of plasma emission spectroscopy, and more particularly relates to improved methods and apparatus for sample aerosol production.

2. Prior Art

In prior art inductively coupled plasma emission spectroscopy, a sample of a substance being analyzed is dissolved in a solvent, and the solution in a controlled chamber is converted by a nebulizer system into an aerosol. The aerosol in a uniform manner is conveyed into a plasma zone from which light signals are emitted that are representative of the substance being analyzed. The procedure can be derived from, for example, the Perkin-Elmer Informationsheft 28, pp. 15–17 (1981).

In the evaluation of the light signals emitted from the plasma after introduction thereinto of aerosol, in simultaneous spectrometry, a relatively small sample solution volume suffices because the optical information of all elements contained therein is simultaneously registered. It is thereby possible to execute multi-element analyses from small solution volumes having high element concentration and to obtain favorable element detection limits. The known disadvantage of the simultaneous spectrometer with photoelectric evaluation is the limitation of the scope of use to analysis lines preliminarily selected.

This disadvantage is avoided in sequential spectrometry in that the analysis lines in the spectrometer, being matched to the respective problem, can also be freely selected and with constant variation. This freedom is acquired at the expense of a higher sample consumption because the analysis lines must be successively selected, and, thus, the emitted light signals from the plasma can likewise not be simultaneously, but only sequentially, recorded. The higher sample consumption therefore requires a greater sample dilution, and, particularly in quantitative multi-element analyses, results in a deterioration of the detection limits of the particular elements being analyzed.

The known nebulizer system for producing an aerosol is described, for example, in an article by G. F. Wallace et al from Paper No. 157 of the Pittsburgh Conference on Analytical Chemistry and Applied Spectroscopy, Atlantic City, N.J., Mar. 8–12, 1982. In such system, only about 10% of the sample amount employed is introduced into the plasma, while, in contrast, about 90% is discharged from a spray chamber unused.

BRIEF SUMMARY OF THE INVENTION

In one aspect, the present invention relates to an improved process for producing an improved aerosol yield from a solution of a sample being analyzed by spectroscopy, for example, by inductively coupled, plasma-emission spectroscopy.

The improved process permits production of a desired aerosol using a minimum amount of starting sample solution.

Also, the improved process permits a multiplicity of sequential usages of the same starting sample liquid for aerosol generation purposes.

In another aspect, the present invention relates to improved apparatus for producing aerosols from sample solutions for use in spectroscopic analysis.

Such apparatus is particularly well adapted for the practice of the process of this invention.

Such apparatus utilizes only relatively small quantities of a given sample solution, yet repeated sequential production of aerosols from that sample solution can be carried out with such apparatus before such quantity is substantially consumed by practicing the inventive process.

A principle object of the present invention is to prevent unutilized sample consumption and thus to increase the aerosol yield in spectroscopy, especially inductively coupled, plasma-emission spectroscopy.

The method and apparatus of this invention utilize a reservoir for the sample liquid and the aerosol formed therefrom. The aerosol is produced in the reservoir from a limited amount of sample liquid with the assistance of an electro-mechanical oscillator system. Only that amount of aerosol thus produced is conveyed by a propellant or carrier gas stream to the plasma that is used for analysis. The unused aerosol is recondensed and returned to the sample liquid. The aerosol production and condensation sequence can be repeated if desired until the initial amount of liquid sample is substantially consumed.

Other and further aims, objects, features, purposes, advantages, embodiments, uses, and the like for the present invention will be apparent to those skilled in the art from the present specification.

BRIEF DESCRIPTION OF DRAWING

In the drawings:

FIG. 1 shows one embodiment of apparatus wherein a piezoceramic oscillator is functionally integrated into a sample solution; and FIG. 2 shows another embodiment of such an apparatus which is similar to that in FIG. 1 except that here the ultrasonic oscillator is functionally operated outside of such a sample solution, such as is desirable when the sample solution incorporates an aggressive component.

DETAILED DESCRIPTION

The invention thereby exploits fluid nebulization by means of ultrasonics which is known from an article by W. D. Drews appearing in the special edition of Elektronik, Volume 28, No. 10, 1979, and which employs a piezoceramic oscillator system for producing the aerosol.

In the Figures, identical reference characters are employed for the identical parts utilized in the respective apparatus embodiments of each of FIGS. 1 and 2.

In the Figures, only that part of a plasma burner 6 essential to the present invention is discussed in detail. Such devices are known to the prior art. The references cited above in the "Background" section of the present specification describe the principles and operation of such a plasma burner.

In FIG. 1, a piezoceramic oscillator 1 is located in the interior bottom region of a reservoir container 8. Oscillator 1 is coupled to an ultrasonic generator 11 by means of electrodes 12. An aerosol 3 is produced from a limited amount of sample liquid 2 situated in the sealable reservoir container 8. Only a portion or sample of this aerosol 3 is swept into the sample tube 5 and led into the plasma burner 6 by a propellant gas stream charged into container 8 through gas tube 4. Thereafter, the aerosol sampling operation is terminated, gas flow through tube 4 is stopped, and oscillator 1 is turned off. The unused aerosol 3 retained in container 8 is thus permitted to recondense and collect in the sample liquid 2. Such liquid 2 is thus available for further treatment by oscillator 1 to generate an aerosol 3 and the sampling process can thus be repeated, as desired. By this procedural sequence, the apparatus shown permits the sample liquid 2 to be almost 100% used for analysis.

FIG. 2, apparatus is shown which is suitable for processing a sample fluid 2 containing an aggressive (reactive) component by means of which, in the FIG. 1 embodiment, the piezoceramic oscillator 1 in contact with such sample liquid 2 could be attacked and damaged. Here, in the FIG. 2 embodiment, an ultrasonic oscillator 7 (a so-called flexural resonator, see the article by W. D. Drews) is employed which is incorporated into a side wall of the reservoir container 8 at a location above the surface of the sample liquid 2. The sample liquid 2 is transported to the ultrasonic oscillator 7 through a suction tube 9 which is connected to a pump 13. If necessary, the ultrasonic oscillator 7 and the tube 9 are provided with a coating of, for example, platinum or the like, which is resistent to the sample liquid 2 and to the aerosol 3 formed therefrom. The apparatus of the FIG. 2 embodiment is otherwise similar to that of the FIG. 1 embodiment.

Thus, the practice of the process of the present invention characteristically involves the utilization of a series of steps. Initially, of course, a quantity of sample liquid 2 which comprises a solution of the substance to be analyzed is charged into a gravitationally lower portion of a sealed chamber or reservoir zone 8. Such quantity is contacted with oscillator 1 using either an arrangement as shown in FIG. 1 or as shown in FIG. 2 (all as described above).

The oscillator 1 is caused to oscillate at an ultrasonic frequency to an extent sufficient to cause formation of an aerosol 3 comprised of a portion of such sample liquid. Such aerosol is located over the surface region of such sample liquid quantity in a gravitationally upper portion of the reservoir zone 8. The exact ultrasonic frequency produced by, and the input power applied to, the oscillator 1 in order to produce such a desired aerosol 3 will, of course, vary from one system to another, being dependent upon many variables, as those skilled in the art will appreciate, such as composition of the sample liquid, the volume or quantity of the sample liquid, the droplet density (or frequency of occurrence thereof) desired in the aerosol 3 formed in the upper portion of reservoir 8, the efficiency of the transducer employed as the oscillator 1, the composition and structure of the wall members of the reservoir 8, and the like.

For purposes of practicing the present invention, it is presently preferred to employ a piezoceramic oscillator which has an applied power conversion efficiency (that is, an efficiency of applied electrical power input into ultrasonic power output) of at least about 80%. It is further presently preferred to employ a reservoir 8 which has an internal volume in the range from about 10 to 200 cubic centimeters, and to charge into such a reservoir initially a volume of sample liquid solution which is in the range from about 2 to 50 cubic centimeters. The solvent employed in such a sample liquid can be any one of the carriers conventionally or typically used in, for example, inductively coupled plasma (ICP) emission spectroscopy; see, for example, the teachings in the above cited Wallace et al article. Conveniently, reservoir 8 can be constructed of quartz, carbon fiber filled polyphenylene sulfide resin (available commercially under the trademark "Ryton" from Phillips Petroleum Company) or the like. Using a volume of sample liquid in the aforeindicated range in a reservoir 8 in the above indicated size range, it is presently preferred to employ an ultrasonic frequency in the range from about 100 to 2500 kilo Hertz applied at a power ranging from about 10 to 500 Watts using an oscillator 1 having the above indicated minimum power conversion efficiency.

The carrier or propellant gas should preferably be inert, as is conventional for nebulizing in the prior art. Examples of suitable such gases include Argon and Nitrogen, and the like. For practicing the invention using parameters such as above illustrated, a carrier gas flow rate through the reservoir 8 conveniently ranges from about 10 to 1000 cubic centimeters per minute, although higher and lower such flow rates may be employed, if desired, as those skilled in the art will appreciate.

In practice, it is presently preferred, using parameters such as above illustrates to apply an excitation oscillation energy to oscillator 1 for a time ranging from about 5 to 50 seconds before carrier gas flow through reservoir 8 at the rates illustratively indicated above is commenced. Conventional solenoid actuated valve arrangements (not shown), or like valve means, are employable to initiate and regulate carrier gas flow. An automated control system can, of course, be employed for regulating process step sequences and conditions, if desired.

As is typical or conventional in the practice of this invention, the aerosol sweeping operation using the carrier gas serves to convey a uniform stream of aerosol from reservoir 8 to the plasma, and such a sweeping is continued, once initiated, for a time interval, which can, for example, range from about 60 to 300 seconds, although longer and shorter sweep times can be employed, if desired, as those skilled in the art will appreciate. During such sweeping, oscillator oscillation is preferably continued, the frequency range illustrated above, in accord with presently preferred practice. Obviously, the shorter the sweep time interval, the greater the quantity of sample liquid left unused reservoir 8 and available for a repeat of the aerosol generation and sweep sequence.

At the end of the sweep period, the carrier gas flow is shut off, and also excitation power to the oscillator 1 is cut off, preferably substantially simultaneously. Within a short time period, illustratively not more than about 2 seconds in the system whose parameters are herein above illustrated at least about 98% by weight of the total residual aerosol is presently believed to have condensed, and the condensate has returned to, the residual volume of sample liquid retained in the lower portion of reservoir 8, such volume being ready for further use in analysis in accord with the principles of this invention, or otherwise if desired.

As is apparent from the foregoing specification, the invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim:

1. A process for producing an aerosol of a sample liquid to be analyzed by means of an inductively coupled plasma emission zone, said process comprising the steps of:

(A) charging a quantity of such a sample liquid into a gravitationally lower portion of a sealed chamber, (B) contacting said sample liquid quantity with an ultrasonic oscillator means, (C) oscillating said oscillator means at an ultrasonic frequency to an extent sufficient to form an aerosol comprised of a portion of said sample liquid in a gravitationally upper portion of said sealed chamber, (D) passing for a predetermined time interval a substantially inert carrier gas into an entry port defined in said sealed chamber, through said upper portion, and out from an exit port defined in said sealed chamber, thereby to sweep a portion of said aerosol in a uniform manner out of said sealed chamber in admixture with said carrier gas, (E) concurrently feeding such mixture of said carrier gas and said aerosol from said sealed chamber into said plasma emission zone, whereby said sample liquid is spectroscopically analyzable, and thereafter (F) terminating said steps (C), (D) and (E) and condensing residual portions of said aerosol which remain in said sealed chamber.

2. The process of claim 1 wherein said steps (C), (D), (E) and (F) are repeated at least once.

3. The process of claim 1 wherein said sample solution comprises a solution of a substance to be so analyzed in a quantity ranging from about 2 to 50 milliliters, and said ultrasonic frequency of said oscillating ranges from about 0.1 to 2500 kilo Hertz applied at a power ranging from about 5 to 500 Watts, said oscillator means having a power conversion efficiency of at least about 50%.

4. The process of claim 1 wherein said oscillator means comprises a piezoceramic oscillator.

5. The process of claim 1 wherein said contacting is achieved by locating said oscillator means in an interior gravitationally bottom portion of said sealed chamber.

6. The process of claim 1 wherein said contacting is achieved by locating said oscillator means in adjacent relationship to said chamber in functional association with said upper portion and by pumping said portion of said sample liquid by conduit means from said lower portion to said oscillator means whereby said oscillator means can convert said sample liquid into said aerosol and release said aerosol into said upper portion.

* * * * *